US00PP35149P3

(12) United States Plant Patent
Snijder

(10) Patent No.: US PP35,149 P3
(45) Date of Patent: May 2, 2023

(54) ***PELARGONIUM* PLANT NAMED 'PEQZ0088'**

(50) Latin Name: ***Pelargonium* x *interspecific***
Varietal Denomination: PEQZ0088

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/826,246

(22) Filed: May 27, 2022

(65) Prior Publication Data

US 2022/0400591 P1 Dec. 15, 2022

(30) Foreign Application Priority Data

Jun. 11, 2021 (QZ) ..... PBR 2021/1577

(51) Int. Cl.
*A01H 5/02* (2018.01)
*A01H 6/42* (2018.01)

(52) U.S. Cl.
USPC ..... Plt./330
CPC ..... *A01H 6/425* (2018.05)

(58) Field of Classification Search
USPC ..... Plt./324, 325, 330
See application file for complete search history.

(56) References Cited

U.S. PATENT DOCUMENTS

PP13,936 P2 * 7/2003 Hofmann ..... A01H 5/02
Plt./330

OTHER PUBLICATIONS https://online.plantvarieties.eu/publicSearch?denomination=peqz0088; CVPO Register—CPVO Application Consulation;version 4.1.85; relieved on Jun. 29, 2022, citation for 'PEQZ0088' (3 pages).*

* cited by examiner

*Primary Examiner* — Susan McCormick Ewoldt
(74) *Attorney, Agent, or Firm* — Dale Skalla

(57) ABSTRACT

A new *Pelargonium* plant named 'PEQZ0088' particularly distinguished by vibrant dark red colored inflorescences with semi-double florets, held above dark green foliage with slight zoning on a vigorous upright plant.

1 Drawing Sheet

Latin name of the genus and species of the plant claimed: *Pelargonium* x *interspecific*.

Varietal denomination: 'PEQZ0088'.

BACKGROUND OF THE NEW PLANT

The present invention comprises a new *Pelargonium*, botanically known as *Pelargonium* x *hortorum*, and hereinafter referred to by the variety name 'PEQZ0088'.

'PEQZ0088' is a product of a planned breeding program. The new cultivar 'PEQZ0088' has vibrant dark red colored inflorescences with semi-double florets, held above dark green foliage with slight zoning on a vigorous upright plant.

'PEQZ0088' originates from a hybridization in a controlled breeding program made in July 2016 in a greenhouse in Enkhuizen, The Netherlands. The female parent was an unpatented plant of *P.* x *hortorum* parentage identified as 'PEZ-AZ3272-07' orange red pigmented florets, when compared to 'PEQZ0088'.

The male parent of 'PEQZ0088' was a patented, proprietary plant of *P.* x *interspecific* parentage, identified as 'PEQZ0015', described in U.S. Plant Pat. No. 28,709 with a lighter green foliage and a more spreading plant habit when compared to 'PEQZ0088'. The resultant seed was sown in January 2017.

'PEQZ0088' was selected as one flowering plant within the progeny of the stated cross in May 2017 in a greenhouse in Enkhuizen, The Netherlands.

The first act of asexual reproduction of 'PEQZ0088' was accomplished when vegetative cuttings were propagated from the initial selection in June 2017 in a greenhouse in Enkhuizen, The Netherlands.

BRIEF SUMMARY OF INVENTION

Horticultural examination of plants grown from cuttings of the plant initiated in June 2017 in Enkhuizen, The Netherlands and continuing thereafter, has demonstrated that the combination of characteristics as herein disclosed for 'PEQZ0088' are firmly fixed and are retained through successive generations of asexual reproduction.

'PEQZ0088' has not been observed under all possible environmental conditions. The phenotype may vary significantly with variations in environment such as temperature, light intensity, and day length.

A Plant Breeder's Right for this cultivar was applied for in the European Union on Jun. 11, 2021, No. 2021/1577. 'PEQZ0088' has not been made publicly available prior to the effective filing date of this application, notwithstanding any disclosure that may have been made less than one year prior to the effective filing date of this application by the inventor or another who obtained 'PEQZ0088' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0088' with colors being as true as possible with an illustration of this type.

Figure 1:
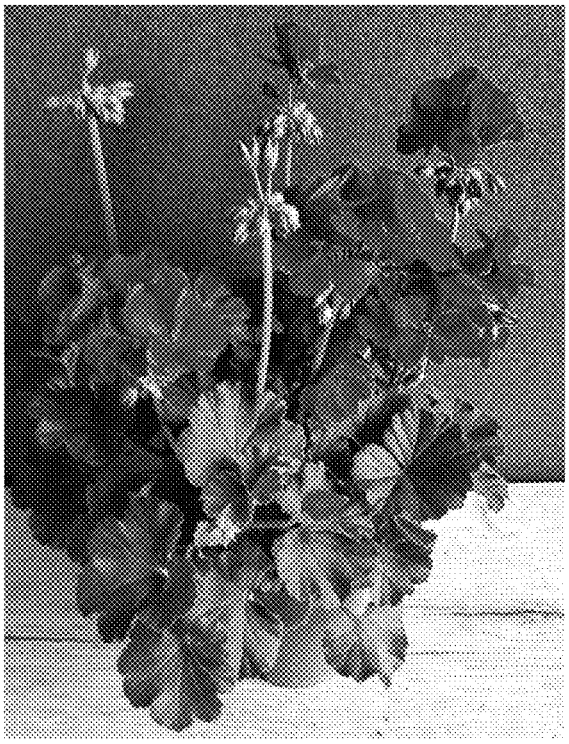
Figure 2:
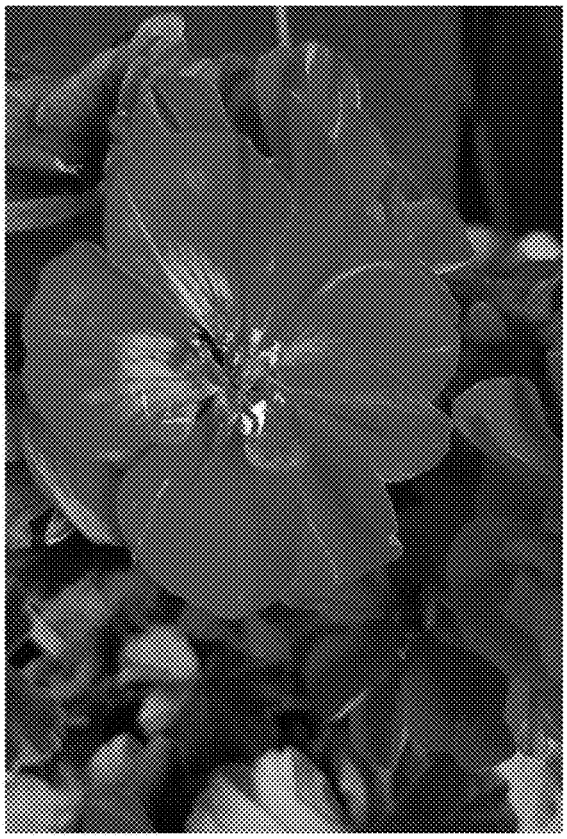

The photographic drawings show in FIG. 1, one flowering plant of the new variety and in FIG. 2, a close-up of an inflorescence.

DETAILED BOTANICAL DESCRIPTION

The plant descriptions and measurements were taken in Enkhuizen, The Netherlands in early June 2021 under natural light. These plants were approximately 16 weeks old and were grown in a 12 cm pots in a greenhouse trial. The plants shown in the photographs were about 16 weeks old growing in a 12 cm pot in a greenhouse. The photographs were taken in June 2021.

Color references are made to The Royal Horticultural Society Colour Chart (R.H.S.) 2001.

TABLE 1

DIFFERENCES BETWEEN THE NEW VARIETY 'PEQZ0088' AND A MOST SIMILAR VARIETY

| | 'PEQZ0088' | 'KLEPZ17484' (U.S. Pat. No. PP30,335) |
|---|---|---|
| Upper color of upper petals: | Red, close to RHS 46B | Red-purple, RHS N57B |
| Color of peduncle: | Green, RHS 144A | Dark greyed-purple, RHS 187A |

Plant:

*Form, growth and habit*.—Mounding, Semi-spreading.
*Plant height*.—17-19 cm.
*Plant height (inflorescence included)*.—24-26 cm.
*Plant width*.—28-32 cm.

Roots:

*Number of days to initiate roots*.—15-18 days at about 22 degrees C.
*Number of days to produce a rooted cutting*.—21-23 days at 22 degrees C.
*Type*.—Fine, fibrous, free branching.
*Color*.—RHS N155B but whiter.

Foliage:

*Variegation*.—Absent.
*Immature leaf, color upper surface*.—Closest to RHS 147A.
*Immature leaf, lower surface*.—Closest to RHS 146A.
*Mature leaf, color upper surface*.—Closest to RHS 147A.
*Mature leaf, color lower surface*.—Closest to RHS 146A.
*Length*.—7-9 cm.
*Width*.—8-11 cm.
*Shape*.—Cordate.
*Base shape*.—Cordate.
*Sinus of mature leaf*.—Very narrow.
*Leaf base openness*.—Open or slightly open, seldom closed.
*Apex shape*.—Rounded.
*Margin*.—Slightly dentate.
*Texture upper side*.—Hirsute.
*Texture lower side*.—Hirsute.
*Leaf zonation color*.—RHS 177A.
*Color of veins, upper surface*.—RHS 147A.
*Color of veins, lower surface*.—RHS 144A.
*Pattern of veining*.—Palmate.
*Petiole color*.—RHS 144A.
*Petiole length*.—5-6 cm.
*Diameter of petiole*.—0.25 cm.
*Texture*.—Pilose, hirsute, glandular hairs.

Stem:

*Quantity of branches*.—5-9.
*Color of stem*.—RHS 143C.
*Anthocyanin coloration of stem*.—No anthocyanin coloration.
*Length of stem*.—9-17 cm.
*Diameter*.—0.5 cm.
*Length of internodes*.—1-6 cm.
*Texture*.—Sparsely hirsute, pilose, glandular hairs.

Peduncle:

*Color of peduncle*.—RHS 144A.
*Length of peduncle*.—10-18 cm.
*Peduncle diameter*.—0.3-0.4 cm.
*Texture*.—Hirsute, glandular hairs.
*Anthocyanin coloration of peduncle*.—Absent.

Pedicel:

*Color of pedicel*.—RHS N77A.
*Length of pedicel*.—2.5-4 cm.
*Diameter of pedicel*.—0.15-0.2 cm.
*Texture*.—Sparsely pilose, glandular hiars.
*Pedicel swelling*.—Swelling was not observed.

Bud (Just before opening):

*Color*.—RHS 46A.
*Length*.—1.0-1.2 cm.
*Width*.—0.7 cm.
*Shape*.—Elliptical.

Inflorescence:

*Type*.—Umbel; semi-spherical or nearly semi-spherical.
*Lastingness of individual flowers*.—7-9 days at 18° C. temperature.
*Number of inflorescences per plant*.—6-12, with 5-12 immature umbels in various stages.
*Average total number of buds*.—24-42.
*Fragrance*.—None.
*Umbel diameter*.—11-13 cm.
*Umbel depth*.—7-9 cm.

Corolla:

*Form*.—Semi-double.
*Number of petals*.—7-9 and 1-3 petaloids.
*Diameter of flower*.—4.5-5.1 cm.
*Depth of flower*.—1.8-2.2 cm.
*Side view shape*.—Concave.
*Color upper petals, upper surface*.—Close to RHS 46B, veins RHS 60A.
*Color upper petals, lower surface*.—Close to RHS 45B, slightly fading to RHS 52B in the center, veins RHS 60A.
*Length of upper petals*.—2.4-2.7 cm.
*Width of upper petals*.—1.5-2.2 cm.
*Color lower petals, upper surface*.—Close to RHS 46B.
*Color lower petals, lower surface*.—Close to RHS 45B, slightly fading to RHS 52B in the center.
*Markings on upper petals*.—Veins RHS 60A.

*Markings on lower petals*.—None.
*Length of lower petals*.—2.3-2.4 cm.
*Width of lower petals*.—2.2-2.3 cm.
*Petal shape*.—Obovate to spathulate.
*Apex shape*.—Rounded.
*Margin*.—Entire.
*Base*.—Attenuate.
*Petal texture*.—Papillose on both surfaces.

Calyx:
*Number of sepals*.—5.
*Color of sepals*.—RHS N144A.
*Length of sepals*.—1.2-1.4 cm.
*Width of sepals*.—0.3-0.5 cm.
*Sepal shape*.—Lanceolate to linear.
*Apex shape*.—Acute.
*Margins*.—Mostly fused.
*Texture, upper surface*.—Glabrous.
*Lower surface*.—Glandular hairs, hirsute.
*Sepal flexing*.—Sepals flexed in mature florets. Upper sepal never flexed.

Reproductive organs:
Gynoecium:
*Pistil*.—Base RHS 138C apex RHS53A.
*Length*.—0.6-0.7 cm.
*Style color*.—RHS 53A.
*Style length*.—0.2 cm.
*Stigma color*.—RHS 53A.
*Ovary color*.—RHS 138C.
*Ovary length*.—0.5 cm.
*Ovary diameter*.—0.2 cm.

Androecium:
*Number of stamens*.—4-6 including petaloids with a developed stamen.
*Color of filaments*.—Base white RHS N157B, tip RHS 51A.
*Length filaments*.—0.5-0.9 cm.
*Anther color*.—RHS 51B.
*Length of anthers*.—0.2 cm.
*Color of pollen*.—RHS 33B.
*Pollen amount*.—Abundant.
*Fertility/seed set*.—Has not been determined to date.
*Disease/pest resistance*.—Has not been determined to date.

What is claimed is:

1. A new and distinct variety of *Pelargonium* plant named 'PEQZ0088' substantially as illustrated and described herein.

* * * * *